United States Patent [19]

Stetter et al.

[11] 4,295,876
[45] Oct. 20, 1981

[54] N-(2,5-DIAZOLYL)-ALKYL-HALOACETANI-LIDES, COMPOUNDS AND HERBICIDAL COMPOSITIONS

[75] Inventors: Jörg Stetter; Klaus Ditgens; Rudolf Thomas, all of Wuppertal; Ludwig Eue, Leverkusen; Robert R. Schmidt, Cologne, all of Fed. Rep. of Germany

[73] Assignee: Bayer Aktiengesellschaft, Leverkusen, Fed. Rep. of Germany

[21] Appl. No.: 143,053

[22] Filed: Apr. 23, 1980

[30] Foreign Application Priority Data

May 12, 1979 [DE] Fed. Rep. of Germany ....... 2919293

[51] Int. Cl.³ .................... A01N 43/64; A01N 43/82; C07D 249/04; C07D 271/08
[52] U.S. Cl. .......................................... 71/90; 71/92; 71/76; 548/101; 548/125; 548/134; 548/135; 548/255
[58] Field of Search .............. 548/101, 125, 134, 135, 548/255; 71/90, 92, 76

[56] References Cited
FOREIGN PATENT DOCUMENTS
2704281 8/1978 Fed. Rep. of Germany ...... 548/262

*Primary Examiner*—Alton D. Rollins
*Attorney, Agent, or Firm*—Sprung, Felfe, Horn, Lynch & Kramer

[57] ABSTRACT

Novel N-(2,5-diazolyl)-alkyl-halogenoacetanilides of the general formula

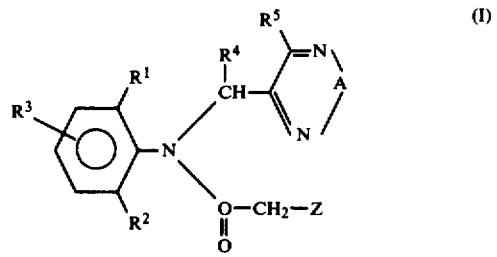

in which
A represents oxygen, sulphur or the grouping >NR,
wherein
R represents alkyl,
$R^1$ represents hydrogen, alkyl or alkoxy,
$R^2$ represents hydrogen, alkyl, alkoxy or halogen,
$R^3$ represents hydrogen, alkyl, alkoxy or halogen,
$R^4$ represents hydrogen or alkyl,
$R^5$ represents hydrogen, alkyl, alkoxy, alkylthio, dialkylamino, halogen, cyano or alkoxycarbonyl and
Z represents halogen, and acid addition salts and metal salt complexes thereof are outstandingly effective as herbicides.

Furthermore novel N-(2,5-diazolyl)-alkyl-anilines of the general formula

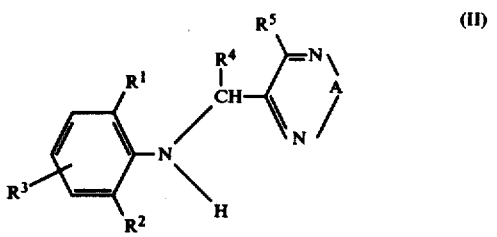

in which $R^1$, $R^2$, $R^3$, $R^4$, $R^5$ and A have the above-mentioned meaning.

38 Claims, No Drawings

N-(2,5-DIAZOLYL)-ALKYL-HALOACETANILIDES, COMPOUNDS AND HERBICIDAL COMPOSITIONS

This invention relates to certain new N-(2,5-diazolyl)-alkyl-haloacetanilide compounds, to herbicidal compositions containing them and to methods of combating undesired vegetation utilizing such compounds.

It is already known that 2,6-diethyl-N-methoxymethylchloroacetanilides can be used for combating weeds (see U.S. Pat. No. 3,442,945). However, this compound is not always completely satisfactory.

The present invention now provides, as new compounds, the N-(2,5-diazolyl)alkyl-haloacetanilides of the formula

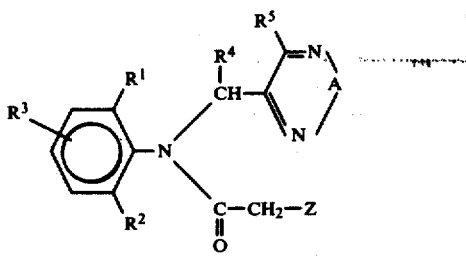

in which

A represents oxygen, sulphur or the grouping >NR, wherein

R represents alkyl, $R^1$ represents hydrogen, alkyl or alkoxy, $R^2$ represents hydrogen, alkyl, alkoxy or halogen, $R^3$ represents hydrogen, alkyl, alkoxy or halogen, $R^4$ represents hydrogen or alkyl, $R^5$ represents hydrogen, alkyl, alkoxy, alkylthio, dialkylamino, halogen, cyano or alkoxycarbonyl and Z represent halogen, and acid addition salts and metal salt complexes thereof.

The invention also provides a process for the preparation of an N-(2,5-diazolyl)alkyl-haloacetanilide of the formula (I) or an acid addition salt or metal salt complex thereof, in which (a) an N-(2,5-diazolyl)alkyl-aniline of the general formula

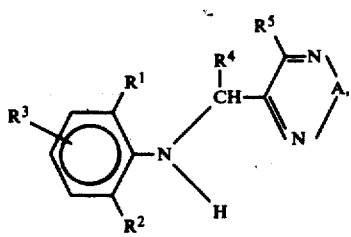

in which A, $R^1$, $R^2$, $R^3$, $R^4$ and $R^5$ have the meanings indicated above, is reacted with a haloacetic acid chloride, bromide or anhydride of the general formula

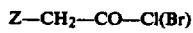

or

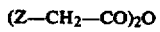

in which Z has the meaning indicated above, in the presence of a diluent and if appropriate in the presence of an acid-binding agent, or (b) a haloacetanilide of the general formula

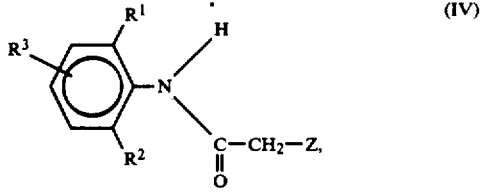

in which $R^1$, $R^2$, $R^3$ and Z have the meanings indicated above, is reacted with a diazolylalkyl derivative of the general formula

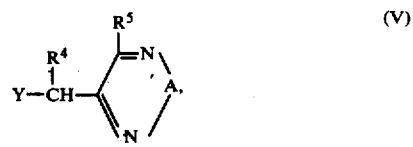

in which A, $R^4$ and $R^5$ have the meanings indicated above and Y represents halogen or the mesyl or tosyl radical, in the presence of an acid-binding agent and if appropriate in the presence of an organic diluent, or in an aqueousorganic two-phase system in the presence of a phase transfer catalyst, and an acid or a metal salt is then optionally added onto the product of process variant (a) and (b).

It has been found that the N-(2,5-diazolyl)alkyl-haloacetanilides of the formula (I) and acid addition salts and metal salt complexes thereof display powerful herbicidal properties, and in particular also selective herbicidal properties. Surprisingly, the N-(2,5-diazolyl) alkyl-haloacetanilides according to the invention display better possibilities for use as agents for selectively combating weeds in important crop plants, coupled with a very good herbicidal action, than 2,6-diethyl-N-methoxymethyl-chloroacetanilide, which is known from the state of the art and is an active compound of high activity and the same type of action. The substances according to the invention thus represent a valuable enrichment of the art.

The preferred N-(2,5-diazolyl)alkyl-haloacetanilides of the formula (I) are those in which A represents oxygen, sulphur or the grouping >NR wherein R represents straight-chain or branched alkyl with 1 to 4 carbon atoms, $R^1$ represents hydrogen or straight-chain or branched alkyl or alkoxy with in either case 1 to 4 carbon atoms, $R^2$ represents hydrogen, straight-chain or branched alkyl or alkoxy with in either case 1 to 4 carbon atoms, fluorine, chlorine or bromine, $R^3$ represents hydrogen, straight-chain or branched alkyl or alkoxy with in either case 1 to 4 carbon atoms, fluorine, chlorine or bromine, $R^4$ represents hydrogen or alkyl with 1 to 4 carbon atoms;

$R^5$ represents hydrogen, straight-chain or branched alkyl with 1 to 4 carbon atoms, straight-chain or branched alkoxy with 1 to 4 carbon atoms, straight-chain or branched alkylthio with 1 to 4 carbon atoms, alkoxycarbonyl with 1 to 4 carbon atoms in the alkoxy group, dialkylamino with 1 to 4 carbon atoms in each alkyl part, fluorine, chlorine, bromine or cyano and Z represents chlorine, bromine or iodine.

Particularly preferred compounds (I) are those in which A represents oxygen, sulphur or the grouping >NR, R representing methyl, ethyl, propyl or butyl; $R^1$ represents hydrogen, methyl, ethyl, isopropyl, sec.-butyl, tert.-butyl, methoxy, ethoxy or isopropoxy; $R^2$ represents hydrogen, methyl, ethyl, isopropyl, sec.-butyl, tert.-butyl, methoxy, ethoxy, isopropoxy, chlorine or bromine; $R^3$ represents hydrogen, methyl, ethyl, isopropyl, sec.-butyl, tert.-butyl, methoxy, ethoxy, isopropoxy, chlorine or bromine; $R^4$ represents hydrogen or methyl, $R^5$ represents hydrogen, methyl, ethyl, n-propyl, isopropyl, n-butyl, sec.-butyl, tert.-butyl, methoxy, ethoxy, isopropoxy, methylthio, ethylthio, isopropylthio, methoxycarbonyl, ethoxycarbonyl, fluorine, chlorine, bromine, cyano, dimethylamino, diethylamino or ethylmethylamino; and Z represents chlorine or bromine.

The following compounds of the general formula (I) may be mentioned specifically, in addition to the compounds mentioned later in the preparative examples:

TABLE 1

(Ia)

| $R^1$ | $R^2$ | $R^3$ | $R^4$ | $R^5$ |
|---|---|---|---|---|
| C(CH$_3$)$_3$ | H | H | H | CH$_3$ |
| CH$_3$ | H | 3-CH$_3$ | H | CH$_3$ |
| CH$_3$ | H | 5-CH$_3$ | H | CH$_3$ |
| CH$_3$ | OCH$_3$ | H | H | CH$_3$ |
| OCH$_3$ | OCH$_3$ | H | H | CH$_3$ |
| CH$_3$ | Cl | H | H | CH$_3$ |
| C(CH$_3$)$_3$ | Cl | H | H | CH$_3$ |
| C$_2$H$_5$ | C$_2$H$_5$ | H | H | H |
| CH$_3$ | C$_2$H$_5$ | H | H | H |
| CH$_3$ | CH$_3$ | H | H | H |
| C(CH$_3$)$_3$ | H | H | H | H |
| CH$_3$ | H | 3-CH$_3$ | H | H |
| CH$_3$ | H | 5-CH$_3$ | H | H |
| CH$_3$ | OCH$_3$ | H | H | H |
| OCH$_3$ | OCH$_3$ | H | H | H |
| CH$_3$ | Cl | H | H | H |
| C(CH$_3$)$_3$ | Cl | H | H | H |
| C$_2$H$_5$ | C$_2$H$_5$ | H | CH$_3$ | CH$_3$ |
| CH$_3$ | C$_2$H$_5$ | H | CH$_3$ | CH$_3$ |
| CH$_3$ | CH$_3$ | H | CH$_3$ | CH$_3$ |
| C(CH$_3$)$_3$ | H | H | CH$_3$ | CH$_3$ |
| CH$_3$ | H | 3-CH$_3$ | CH$_3$ | CH$_3$ |
| CH$_3$ | H | 5-CH$_3$ | CH$_3$ | CH$_3$ |
| CH$_3$ | OCH$_3$ | H | CH$_3$ | CH$_3$ |
| OCH$_3$ | OCH$_3$ | H | CH$_3$ | CH$_3$ |
| CH$_3$ | Cl | H | CH$_3$ | CH$_3$ |
| C(CH$_3$)$_3$ | Cl | H | CH$_3$ | CH$_3$ |
| C$_2$H$_5$ | C$_2$H$_5$ | H | CH$_3$ | H |
| CH$_3$ | C$_2$H$_5$ | H | CH$_3$ | H |
| CH$_3$ | CH$_3$ | H | CH$_3$ | H |
| C$_2$H$_5$ | C$_2$H$_5$ | H | H | C$_2$H$_5$ |
| CH$_3$ | C$_2$H$_5$ | H | H | C$_2$H$_5$ |
| CH$_3$ | CH$_3$ | H | H | C$_2$H$_5$ |
| C$_2$H$_5$ | C$_2$H$_5$ | H | H | Cl |
| CH$_3$ | C$_2$H$_5$ | H | H | Cl |
| CH$_3$ | CH$_3$ | H | H | Cl |
| C$_2$H$_5$ | C$_2$H$_5$ | H | H | OCH$_3$ |
| CH$_3$ | C$_2$H$_5$ | H | H | OCH$_3$ |
| CH$_3$ | CH$_3$ | H | H | OCH$_3$ |
| C$_2$H$_5$ | C$_2$H$_5$ | H | H | SCH$_3$ |

TABLE 1-continued (Ia)

| $R^1$ | $R^2$ | $R^3$ | $R^4$ | $R^5$ |
|---|---|---|---|---|
| CH$_3$ | C$_2$H$_5$ | H | H | SCH$_3$ |
| CH$_3$ | CH$_3$ | H | H | SCH$_3$ |

TABLE 2

(Ib)

| $R^1$ | $R^2$ | $R^3$ | $R^4$ | $R^5$ |
|---|---|---|---|---|
| C(CH$_3$)$_3$ | H | H | H | CH$_3$ |
| CH$_3$ | H | 3-CH$_3$ | H | CH$_3$ |
| CH$_3$ | H | 5-CH$_3$ | H | CH$_3$ |
| CH$_3$ | OCH$_3$ | H | H | CH$_3$ |
| OCH$_3$ | OCH$_3$ | H | H | CH$_3$ |
| CH$_3$ | Cl | H | H | CH$_3$ |
| C(CH$_3$)$_3$ | Cl | H | H | CH$_3$ |
| C(CH$_3$)$_3$ | H | H | CH$_3$ | CH$_3$ |
| CH$_3$ | H | 3-CH$_3$ | CH$_3$ | CH$_3$ |
| CH$_3$ | H | 5-CH$_3$ | CH$_3$ | CH$_3$ |
| CH$_3$ | OCH$_3$ | H | CH$_3$ | CH$_3$ |
| OCH$_3$ | OCH$_3$ | H | CH$_3$ | CH$_3$ |
| CH$_3$ | Cl | H | CH$_3$ | CH$_3$ |
| C(CH$_3$)$_3$ | Cl | H | CH$_3$ | CH$_3$ |
| C$_2$H$_5$ | C$_2$H$_5$ | H | CH$_3$ | H |
| CH$_3$ | C$_2$H$_5$ | H | CH$_3$ | H |
| CH$_3$ | CH$_3$ | H | CH$_3$ | H |
| C$_2$H$_5$ | C$_2$H$_5$ | H | H | C$_2$H$_5$ |
| CH$_3$ | C$_2$H$_5$ | H | H | C$_2$H$_5$ |
| CH$_3$ | CH$_3$ | H | H | C$_2$H$_5$ |
| C$_2$H$_5$ | C$_2$H$_5$ | H | H | Cl |
| CH$_3$ | C$_2$H$_5$ | H | H | Cl |
| CH$_3$ | CH$_3$ | H | H | Cl |
| C$_2$H$_5$ | C$_2$H$_5$ | H | H | OCH$_3$ |
| CH$_3$ | C$_2$H$_5$ | H | H | OCH$_3$ |
| CH$_3$ | CH$_3$ | H | H | OCH$_3$ |
| C$_2$H$_5$ | C$_2$H$_5$ | H | H | SCH$_3$ |
| CH$_3$ | C$_2$H$_5$ | H | H | SCH$_3$ |
| CH$_3$ | CH$_3$ | H | H | SCH$_3$ |

TABLE 3

(Ic)

| $R^1$ | $R^2$ | $R^3$ | $R^4$ | $R^5$ | R |
|---|---|---|---|---|---|
| CH$_3$ | CH$_3$ | H | H | H | CH$_3$ |
| CH$_3$ | C$_2$H$_5$ | H | H | H | CH$_3$ |
| C$_2$H$_5$ | C$_2$H$_5$ | H | H | H | CH$_3$ |

TABLE 3-continued

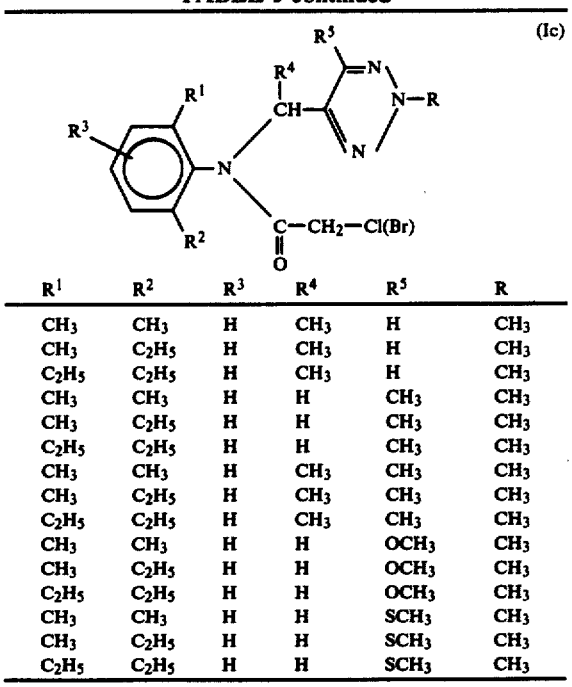

(Ic)

| R¹ | R² | R³ | R⁴ | R⁵ | R |
|---|---|---|---|---|---|
| CH₃ | CH₃ | H | CH₃ | H | CH₃ |
| CH₃ | C₂H₅ | H | CH₃ | H | CH₃ |
| C₂H₅ | C₂H₅ | H | CH₃ | H | CH₃ |
| CH₃ | CH₃ | H | H | CH₃ | CH₃ |
| CH₃ | C₂H₅ | H | H | CH₃ | CH₃ |
| C₂H₅ | C₂H₅ | H | H | CH₃ | CH₃ |
| CH₃ | CH₃ | H | CH₃ | CH₃ | CH₃ |
| CH₃ | C₂H₅ | H | CH₃ | CH₃ | CH₃ |
| C₂H₅ | C₂H₅ | H | CH₃ | CH₃ | CH₃ |
| CH₃ | CH₃ | H | H | OCH₃ | CH₃ |
| CH₃ | C₂H₅ | H | H | OCH₃ | CH₃ |
| C₂H₅ | C₂H₅ | H | H | OCH₃ | CH₃ |
| CH₃ | CH₃ | H | H | SCH₃ | CH₃ |
| CH₃ | C₂H₅ | H | H | SCH₃ | CH₃ |
| C₂H₅ | C₂H₅ | H | H | SCH₃ | CH₃ |

Preferred compounds according to the invention are also addition products of acids and those N-(2,5-diazolyl)-alkyl-haloacetanilides of the formula (I) in which A, R¹, R², R³, R⁴, R⁵ and Z have the meanings which have already been mentioned as preferred. The acids which can be added on include, as preferences, hydrogen halide acids (for example hydrobromic acid and in particular hydrochloric acid), phosphoric acid, nitric acid, sulphuric acid, monofunctional and bifunctional carboxylic acids and hydroxycarboxylic acids (for example acetic acid, maleic acid, succinic acid, fumaric acid, tartaric acid, citric acid, salicylic acid, sorbic acid and lactic acid) and sulphonic acids (for example p-toluenesulphonic acid and 1,5-naphthalenedisulphonic acid).

Compounds according to the invention which are also preferred are addition products of salts of metals of main groups II to IV and of sub-groups I and II and IV to VIII of the period system and those N-(2,5-diazolyl)alkyl-haloacetanilines of the formula (I) in which A, R¹, R², R³, R⁴, R⁵ and Z have the meanings which have already been mentioned as preferred. Salts of copper, zinc, manganese, magnesium, tin, iron and nickel are particularly preferred in this context. Possible anions of these salts are those which are derived from those acids which lead to physiologically acceptable addition products. Particularly preferred acids in this connection are the hydrogen halide acids (for example hydrochloric acid and hydrobromic acid), phosphoric acid, nitric acid and sulphuric acid.

If 2-ethyl-6-methyl-N-(4-methyl-1,2,5-thiadiazol-3-yl-methyl)-aniline and chloroacetyl chloride are used as starting substances in process variant (a), the course of the reaction can be represented by the following equation:

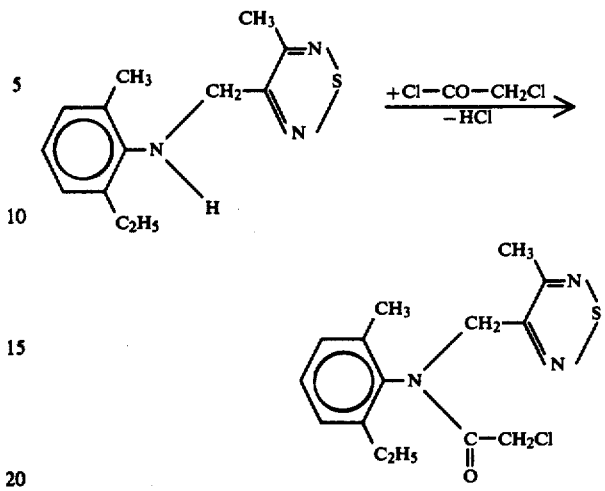

If 2,6-dimethyl-chloroacetanilide and 3-bromo-methyl-4-methyl-1,2,5-oxadiazole are used as starting substances in process variant (b), the course of the reaction can be represented by the following equation:

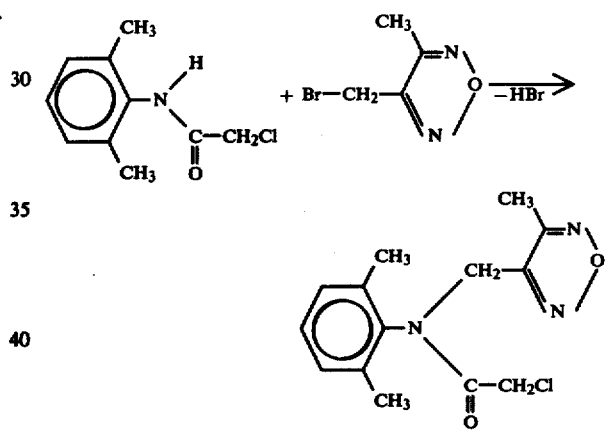

The formula (II) provides a general definition of the N-(2,5-diazolyl)-alkyl-anilines required as starting substances in carrying out process variant (a). In this formula, A, R¹, R², R³, R⁴ and R⁵ preferably have those meanings which have already been mentioned as preferred in connection with the description of the substances of the formula (I).

The N-(2,5-diazolyl)alkyl-anilines of the formula (II) have not hitherto been described in the literature. They are obtained when anilines of the general formula

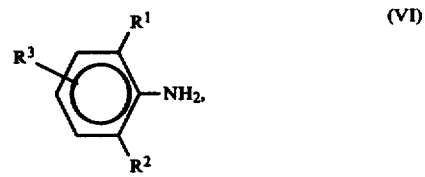

(VI)

in which R¹, R² and R³ have the meanings indicated above, are reacted with diazolylalkyl derivatives of the general formula

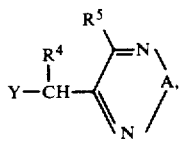

in which A, $R^4$, $R^5$ and Y have the meanings indicated above, in the presence of an acid-binding agent and if appropriate in the presence of a diluent.

The anilines of the formula (VI) required as starting substances in the preparation of the N-(2,5-diazolyl)alkylanilines of the formula (II) are generally known compounds of organic chemistry. Examples which may be mentioned are: aniline, 2-methylaniline, 2-ethylaniline, 2-isopropylaniline, 2-sec.-butylaniline, 2-tert.-butylaniline, 2,6-dimethylaniline, 2,3-dimethylaniline, 2,5-dimethylaniline, 3,5-dimethylaniline, 2,6-diethylaniline, 2-ethyl-6-methylaniline, 2,3,4-trimethylaniline, 2,4,6-trimethylaniline, 2,4,5-trimethylaniline, 2-ethyl-4,6-dimethylaniline, 2,6-diethyl-4-methylaniline, 2,6-diisopropyl-4-methylaniline, 2,3,5-trimethylaniline, 2,3,6-trimethylaniline, 2-methyl-6-chloroaniline, 2-tert.-butyl-6-chloroaniline, 2-methoxy-6-methylaniline, 2,6-dimethoxyoxyaniline, 2-methoxy-6-ethoxyaniline and 2,6-diethoxyaniline.

Any of the customary acid acceptors can be used as acid-binding agents in the preparation of the N-(2,5-diazolyl)alkyl-anilines of the formula (II). Alkali metal carbonates, such as potassium carbonate or sodium carbonate, are preferably used.

Any of the customary inert organic solvents can be employed as diluents in the preparation of the N-(2,5-diazolyl)alkylonilines of the formula (II). Dimethylformamide and toluene are preferably used.

The reaction temperatures can be varied within a subtantial range in the preparation of the N-(2,5-diazolyl)alkylanilines of the formula (II) by the above process. In general, the reaction is carried out at between 0° C. and 180° C., preferably between 20° C. and 160° C.

In the preparation of the N-(2,5-diazolyl)alkylanilines of the formula (II) by the above process, the anilines of the formula (VI) and the diazolylalkyl derivatives of the formula (V) are in general employed in equimolar amounts. However, it is also possible to employ one of the components, preferably the aniline of the formula (VI), in excess. Working up and isolation of the reaction products are effected by customary methods (see also the preparative examples).

The formulae (IIIa) and (IIIb) provide general definitions of the haloacetic acid chlorides, bromides and anhydrides also to be used as starting substances for process variant (a). In these formulae, Z preferably represents chlorine, bromine or iodine.

The haloacetic acid chlorides, bromides and anhydrides of the formulae (IIIa) and (IIIb) are generally known compounds of organic chemistry. Examples which may be mentioned are: chloroacetyl chloride, bromoacetyl chloride, iodoacetyl chloride and the corresponding bromides and anhydrides.

The formyla (IV) provides a general definition of the haloacetanilides required as starting substances in carrying out process variant (b). In this formula, $R^1$, $R^2$, $R^3$ and Z preferably have those meanings which have already been mentioned as preferred in connection with the description of the substances of the formula (I).

The haloacetanilides of the formula (IV) are generally known, or they can be obtained in a generally known manner, be reacting corresponding anilines with a haloacetic acid chloride, bromide or anhydride of the formula (IIIa) or (IIIb) in the presence of an inert organic solvent, for example toluene or dimethylformamide, if appropriate in the presence of an acid-binding agent, for example potassium carbonate or triethylamine, at temperatures between 0° C. and 100° C. (see also the preparative examples). The chloroacetanilides and the bromoacetanilides of the anilines of the formula (VI) indicated above may be mentioned as examples.

The formula (V) provides a general definition of the diazolylalkyl derivatives also to be used as starting substances for process variant (b). In this formula, A, $R^4$ and $R^5$ preferably have those meanings which have already been mentioned as preferred in connection with the description of the substances of the formula (I). Y preferably represents chlorine, bromine or the mesyl or tosyl radical.

The diazolyl derivatives of the formula (V) are known in some cases (see J. Heterocyclic Chem. 4, 445–46 (1967)), or they can be obtained in a generally known manner, for example by replacing the active hydrogen atom in diazolyl derivatives of the general formula

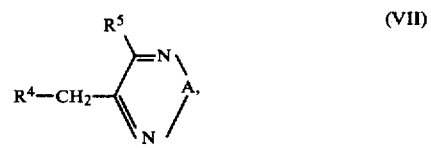

in which A, $R^4$ and $R^5$ have the meanings indicated above, by halogen in the customary manner, for example by reaction with N-bromosuccinimide (see also preparative examples).

The diazolyl derivatives of the formula (V) can also be obtained if 3-carboxylic acid ester derivatives of the diazolyl derivatives of the formula (VII) are reduced to the corresponding 3-hydroxymethyl-diazolyl derivatives and these are reacted with a halogenating agent, for example thionyl chloride or phosphorus tribromide, or with a sulphonylating agent, such as mesyl chloride or tosyl chloride, if appropriate in the presence of an inert organic solvent, at a temperature between −20° C. and +50° C.

The diazolyl derivatives of the formula (VII) are known (see, inter alia, Journal of Organic Chemistry, 32, 2823 et seq. (1967); or they can be obtained by customary synthesis methods for heterocyclic compounds.

Preferred diluents for the reaction in process variant (a) are inert organic solvents. These include, as preferences, ketones, such as diethyl ketone, and in particular acetone and methyl ethyl ketone; nitriles; such as proprionitrile, and in particular acetonitrile; ethers, such as tetrahydrofuran or dioxan; aliphatic and aromatic hydrocarbons, such as petroleum ether, benzene, toluene or xylene; halogenated hydrocarbons, such as methylene chloride, carbon tetrachloride, chloroform or chlorobenzene, and esters, such as ethyl acetate.

If appropriate, process variant (a) can be carried out in the presence of an acid-binding agent (for example hydrogen chloride acceptor). Any of the customary acid-binding agents can be used here. These include, as preferences, such organic bases as tertiary amines, for example triethylamine or pyridine, and furthermore such inorganic bases as alkali metal hydroxides and alkali metal carbonates.

The reaction temperatures can be varied within a substantial range in carrying out process variant (a). In general, the reaction is carried out at from 0° C. to 120° C., preferably from 20° C. to 100° C.

In carrying out process variant (a), 1 to 1.5 moles of haloacetylating agent and 1 to 1.5 moles of acid-binding agent are preferably employed per mole of the compound for the formula (II). The resultant compound of the formula (I) is isolated in the customary manner.

Possible diluents for the reaction in process variant (b) are any of the inert, water-immiscible, organic solvents. These include, as preferences, ethers, such as diethyl ether; aromatic hydrocarbons, such as benzene, toluene or xylene; halogenated hydrocarbons, such as methylene chloride, carbon tetrachloride, chloroform or chlorobenzene; and esters, such as ethyl acetate.

The reaction in process variant (b) is carried out in the presence of an acid-binding agent. Any of the customary acid-binding agents can be used here. These include, as preferences, inorganic bases, for example alkali metal hydroxides and alkali metal carbonates.

The reaction temperatures can be varied within a substantial range in carrying out process variant (b). In general, the reaction is carried out at from −70° C. to +100° C., preferably from −20° C. to +80° C.

In carrying out process variant (b), 1 to 1.5 moles of diazolyl-alkyl derivative of the formula (V) are preferably employed per mole of haloacetanilide of the formula (IV). The resultant compound of the formula (I) is isolated in the customary manner.

In a preferred embodiment, the reaction in process (b) is carried out in a two-phase system, for example aqueous sodium hydroxide solution or potassium hydroxide solution/toluene or methylene chloride, if appropriate with the addition of 0.1–1 mole of a phase transfer catalyst, for example an ammonium or phosphonium compound, benzyldodecyl-dimethyl-ammonium chloride (Zephirol) and triethylbenzyl-ammonium chloride being mentioned as examples (see also the preparative examples).

Also, the substances of the formula (I) which can be prepared by process variants (a) and (b) can be converted into acid addition salts or metal salt complexes.

The following acids can preferably be used for the preparation of physiologically acceptable acid addition salts of the compounds of the formula (I): hydrogen halide acids (for example hyrobromic acid and in particular hydrochloric acid), phosphoric acid, nitric acid, sulphuric acid, monofunctional and bifunctional carboxylic acids and hydroxycarboxylic acids (for example acetic acid, maleic acid, succinic acid, fumaric acid, tartaric acid, citric acid, salicylic acid, sorbic acid and lactic acid) and sulphonic acids (for example p-toluenesulphonic acid and 1,5-naphthalenedisulphonic acid).

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and if appropriate purified by washing with an inert organic solvent.

Salts of metals of main groups II to IV and of subgroups I and II and IV to VIII of the periodic system can preferably be used for the preparation of metal salt complexes of the compounds of the formula (I), examples of metals which may be mentioned being copper, zinc, manganese, magnesium, tin, iron and nickel.

Preferred anions of the salts are those which are derived from the following acids: hydrogen halide acids (for example hydrochloric acid and hydrobromic acid), phosphoric acid, nitric acid and sulphuric acid.

The metal salt complexes of the compounds of the formula (I) can be obtained in a simple manner by customary processes, for example by dissolving the metal salt in alcohol, for example ethanol, and adding this solution to the compounds of the formula (I). The metal salt complexes can be purified in a known manner, for example by filtration, isolation and, if appropriate, by recrystallization.

The active compounds according to the invention influence plant growth and can therefore be used as defoliants, desiccants, agents for destroying broad-leaved plants, germination inhibitors and, especially, as weed-killers. By "weeds" in the broadest sense there are meant plants growing in places where they are not desired.

Whether the compounds according to the invention act as total herbicides or selective herbicides depends essentially on the amount used.

The active compounds according to the present invention may be used, for example, to combat the following plants:

dicotyledon weeds of the genera Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Rorippa, Rotala, Lindernia, Lamium, Veronica, Abutilon, Emex, Datura, Viola, Galeopsis, Papaver, Centaurea and Solanum; and monocotyledon weeds of the genera Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochloria, Fimbristylis, Sagittaria, Eleocharis, Scirpus, Paspalum, Ischaemum, Sphenoclea, Dactyloctenium, Agrostis, Alopecurus and Apera.

The active compounds according to the present invention may be used, for example, as selective herbicides in the following cultures:

dicotyledon cultures of the genera Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita; and monocotyledon cultures of the genera Oryza, Zea, Triticum, Hordeum, Avena, Secale, Sorghum, Panicum, Saccharum, Ananas, Asparagus and Allium.

However, the use of the active compounds according to the invention is in no way restricted to these genera but also embraces other plants, in the same way.

Depending on the concentrations, the compounds can be used for the total combating of weeds, for example on industrial terrain and railway tracks and on paths and squares with or without trees. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cacao plantations, soft fruit plantings and hopfields, and for the selective combating of weeds in annual cultures.

In particular, in addition to a very good action against grasses and against Cyperus varieties, the active compounds according to the invention also exhibit a good herbicidal action against broad-leaved weeds. The possibilities of using the active compounds according to the invention selectively, preferably in maize, sugar beet, soya bean and cotton, should be emphasized.

When certain amounts are applied, the substances according to the invention also exhibit a growth regulating action, especially growth inhibition, and a fungicidal action, especially against Oomycetes, and *Pyricularia oryzae* in rice.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is to say, liquid or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention, as such or in the form of their formulations, can also be used, for combating weeds, as mixtures with known herbicides, finished formulations or tank mixing being possible. Mixtures with other active compounds, such as fungicides, insecticides, acaricides, nematicides, bird repellants, growth factors, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They may be used in the customary manner, for example by watering, spraying, atomizing or scattering.

The active compounds according to the invention can be applied either before or after emergence of the plants. They are preferably applied before emergence of the plants, that is to say by the pre-emergence method. They can also be incorporated into the soil before sowing.

The amount of active compound used can vary within a substantial range. It depends essentially on the nature of the desired effect. In general, the amounts used are from 0.1 to 10 kg of active compound per ha, preferably from 0.25 to 5 kg/ha.

The present invention also provides a herbicidal composition containing as active ingredient a compound of the present invention in admixture with a solid diluent or carrier or in admixture with a liquid diluent or carrier containing a surface-active agent.

The present invention also provides a method of combating weeds which comprises applying to the weeds, or to a habitat thereof, a compound of the present invention alone or in the form of a composition containing as active ingredient a compound of the present invention in admixture with a diluent or carrier.

The present invention further provides crops protected from damage by weeds by being grown in areas in which immediately prior to and/or during the time of the growing a compound of the present invention was applied alone or in admixture with a diluent or carrier.

It will be seen that the usual methods of providing a harvested crop may be improved by the present invention.

The herbicidal activity of the compounds of this invention is illustrated by the following biotest Example.

In this Example, the compounds according to the present invention are each identified by the number (given in brackets) of the corresponding preparative Example, which will be found later in this specification.

The known comparison compound is identified as follows:

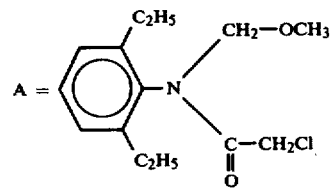

(2,6-Diethyl)-N-methoxymethyl-chloroacetanilide

EXAMPLE A

Pre-emergence test
Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

Seeds of the test plants were sown in normal soil and, after 24 hours, watered with the preparation of the active compound. It was expedient to keep constant the amount of water per unit area. The concentration of the active compound in the preparation was of no importance, only the amount of active compound applied per unit area being decisive. After three weeks, the degree of damage to the plants was determined in % damage in comparison to the development of the untreated control. The figures denoted:
0% = no action (like untreated control)
100% = total destruction In this test, the active compounds (1), (3), (4), (7) and (8) exhibited a better selective herbicidal activity than the substance (A) known from the prior art.

PREPARATIVE EXAMPLES

EXAMPLE 1

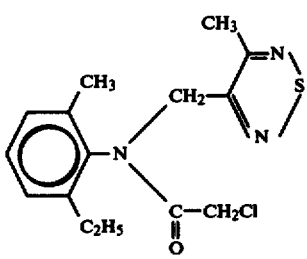

(1)

Process variant (a)

59 g (0.239 mol) of 2-ethyl-6-methyl-N-(4-methyl-1,2,5-thiadiazol-3-yl-methyl)-aniline and 20 g (0.25 mol) of pyridine were dissolved in 200 ml of absolute tetrahydrofuran, and 28.25 g (0.25 mol) of chloroacetyl chloride were added dropwise, while stirring. During this addition, the internal temperature rose to 60° C. Stirring was then continued at room temperature for 1 hour. Thereafter, the reaction solution was concentrated and water was added. The crystalline reaction product was filtered off and washed with water. After drying, 70.5 g (91% of theory) of 2-ethyl-6-methyl-N-(4-methyl-1,2,5-thiadiazol-3-yl-methyl)-chloroacetanilide were obtained as a beige-colored powder of melting point 89°-93° C.

Preparation of the precursors

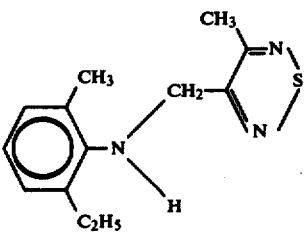

(II-1)

A mixture of 68 g (0.652 mol) of 2-ethyl-6-methylaniline, 45 g (0.326 mol) of powdered potassium carbonate and 30 ml of dimethylformamide was heated to 100° C. and 63 g (0.326 mol) of 3-bromomethyl-4-methyl-1,2,5-thiadiazole were added dropwise, while stirring. The mixture was stirred at 100° C. for a further 5 hours, the inorganic precipitate was filtered off and the filtrate was distilled. 59.4 g (77.4% of theory) of 2-ethyl-6-methyl-N-(4-methyl-1,2,5-thiadiazol-3-yl-methyl)-aniline of boiling point 160°-163° C./0.3 mm Hg were obtained.

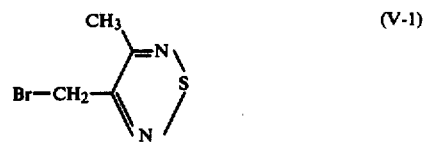

(V-1)

30 g (0.263 mol) of 3,4-dimethyl-1,2,5-thiadiazole and 46.8 g (0.263 mol) of 4-bromosuccinimide, with the addition of 100 mg of azodiisobutyronitrile in 200 ml of absolute carbon tetrachloride, were heated under reflux. The succinimide formed was then filtered off and the filtrate was distilled. 25.3 g (50% of theory) of 3-bromomethyl-4-methyl-1,2,5-thiadiazole of boiling point 50°-56° C./0.1 mm Hg were obtained.

EXAMPLE 2

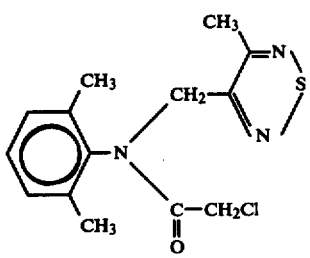

(2)

Process variant (b)

5.2 g of 3-bromomethyl-4-methyl-1,2,5-thiadiazole were rapidly added dropwise to a rapidly stirred 2-phase mixture of 4.5 g (0.022 mol) of 2,6-dimethylchloroacetanilide, 200 ml of triethylbenzylammonium chloride, 25 ml of 50% strength sodium hydroxide solution and 100 ml of methylene chloride at room temperature. After stirring the mixture for 1 hour, the organic phase was separated off, washed several times with water, dried over sodium sulphate and concentrated. The crystalline crude product was recrystallized from petroleum ether. 3.5 g (51% of theory) of 2,6-dimethyl-N-(4-methyl-1,2,5-thiadiazol-3-ylmethyl)-chloroacetanilide of melting point 84°-85° C. were obtained.

EXAMPLE 3

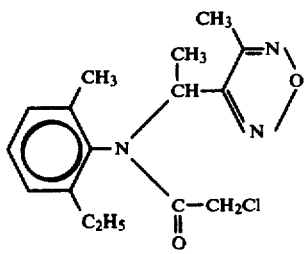

Process variant (a)

14.5 g (0.06 mol) of 2-ethyl-6-methyl-N-(4-methyl-1,2,5-oxadiazol-3-yl-eth-1-yl)-aniline and 4.75 g (0.06 mol) of pyridine in 100 ml of absolute tetrahydrofuran were heated to the boiling point and 6.8 g (0.06 mol) of chloroacetyl chloride were added dropwise, while stirring. When the addition had ended, the reaction mixture was stirred under reflux for 5 minutes and concentrated, the residue was taken up in methylene chloride and the methylene chloride mixture was extracted by shaking with water. The organic phase was dried over sodium sulphate and concentrated. After purification of the residue over a silica gel column and recrystallization of the product from petroleum ether, 9.6 g (49.8% of theory) of 2-ethyl-6-methyl-N-(4-methyl-1,2,5-oxadiazol-3-yl-eth-1-yl)-chloroacetanilide of melting point 91°–92° C. were obtained.

Preparation of the precursors

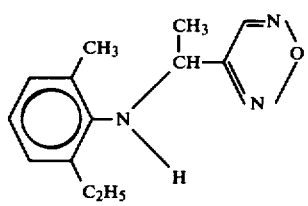
(II-2)

14.8 g (75.5% of theory) of 2-ethyl-6-methyl-N-(4-methyl-1,2,5-oxadiazol-3-yl-eth-1-yl)-aniline, which was further reacted directly, were obtained, analogously to the procedure described in Example 1 for compound (II-1), from 10.8 g (0.08 mol) of 2-ethyl-6-methyl-aniline, 11.0 g (0.08 mol) of powdered potassium carbonate and 15.3 g (0.08 mol) of 3-(1-bromo-eth-1-yl)-4-methyl-1,2,5-oxadiazole.

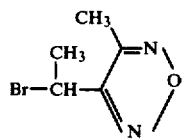
(V-2)

14.1 g (61.5% of theory) of 3-(1-bromo-eth-1-yl)-4-methyl-1,2,5-oxadiazole of boiling point 76° C./12 mm Hg were obtained, analogously to the procedure described after Example 1 in respect of the compound (V-1), from 13.5 g (0.12 mol) of 3-ethyl-4-methyl-1,2,5-oxadiazole and 21.4 g (0.12 mol) of N-bromosuccinimide, with the addition of 0.2 g of azodiisobutyronitrile in 150 ml of absolute carbon tetrachloride.

Those compounds listed in Table 4 were obtained analogously to Example 1, 2 or 3.

TABLE 4

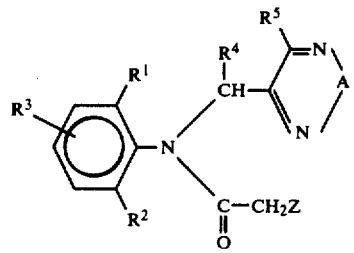

| Example No. | $R^1$ | $R^2$ | $R^3$ | $R^4$ | $R^5$ | A | Z | Melting point (°C.) |
|---|---|---|---|---|---|---|---|---|
| 4 | $C_2H_5$ | $C_2H_5$ | H | H | $CH_3$ | S | Cl | Oil |

TABLE 4-continued

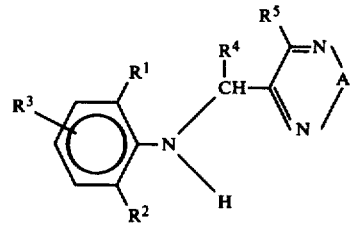

| Example No. | $R^1$ | $R^2$ | $R^3$ | $R^4$ | $R^5$ | A | Z | Melting point (°C.) |
|---|---|---|---|---|---|---|---|---|
| 5 | $CH_3$ | $CH_3$ | H | $CH_3$ | $CH_3$ | O | Cl | 124–26 |
| 6 | $C_2H_5$ | $C_2H_5$ | H | $CH_3$ | $CH_3$ | O | Cl | 72 |
| 7 | $CH_3$ | $C_2H_5$ | H | H | $CH_3$ | O | Cl | Oil |
| 8 | $CH_3$ | $CH_3$ | H | H | $CH_3$ | O | Cl | 79–80 |
| 9 | $C_2H_5$ | $C_2H_5$ | H | H | $CH_3$ | O | Cl | 80–82 |
| 10 | $CH_3$ | $CH_3$ | H | $C_2H_5$ | $CH_3$ | O | Cl | 113 |

The starting materials of the formula (II) listed in Table 5 below were obtained by the process described in the Application, analogously to the procedures described after Examples 1 and 3:

TABLE 5

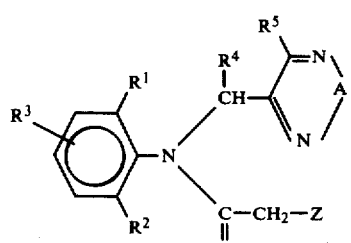

| No. | $R^1$ | $R^2$ | $R^3$ | $R^4$ | $R^5$ | A | Physical constants |
|---|---|---|---|---|---|---|---|
| (II-3) | $CH_3$ | $CH_3$ | H | H | $CH_3$ | S | not isolated |
| (II-4) | $C_2H_5$ | $C_2H_5$ | H | H | $CH_3$ | S | boiling point 130–140° C./0.1 |
| (II-5) | $CH_3$ | $CH_3$ | H | $CH_3$ | $CH_3$ | O | not isolated |
| (II-6) | $C_2H_5$ | $C_2H_5$ | H | $CH_3$ | $CH_3$ | O | not isolated |
| (II-7) | $CH_3$ | $C_2H_5$ | H | H | $CH_3$ | O | not isolated |
| (II-8) | $CH_3$ | $CH_3$ | H | H | $CH_3$ | O | not isolated |
| (II-9) | $C_2H_5$ | $C_2H_5$ | H | H | $CH_3$ | O | not isolated |

It will be understood that the specification and examples are illustrative, but not limitative of the present invention and that other embodiments within the spirit and scope of the invention will suggest themselves to those skilled in the art.

What is claimed is:

1. N-(2,5-diazolyl) alkyl-haloacetanilide compounds of the formula wherein

A is oxygen, sulfur or the grouping >N-R in which R is alkyl with up to 4 carbon atoms;

R$^1$ is hydrogen, alkyl with up to 4 carbon atoms, or alkoxy with up to 4 carbon atoms;

R$^2$ is hydrogen, alkyl with up to 4 carbon atoms, alkoxy with up to 4 carbon atoms, or fluorine, chlorine, or bromine;

R$^3$ is hydrogen, alkyl with up to 4 carbon atoms, alkoxy with up to 4 carbon atoms, or fluorine, chlorine or bromine;

R$^4$ is hydrogen or alkyl with up to 4 carbon atoms;

R$^5$ is hydrogen, alkyl with up to 4 carbon atoms, alkoxy with up to 4 carbon atoms, dialkylamino with up to 4 carbon atoms in each alkyl group, fluorine, chlorine or bromine, cyano or alkoxycarbonyl with up to 4 carbon atoms in the alkoxy group; and Z is chlorine, bromine or iodine.

2. Compound as claimed in claim 1 in which A is oxygen.

3. Compound as claimed in claim 1 in which A is sulfur.

4. Compound as claimed in claim 1 wherein A is >N-R, in which R is alkyl of up to 4 carbon atoms.

5. Compound as claimed in claim 1 wherein R$^1$ is hydrogen.

6. Compound as claimed in claim 1 wherein R$^1$ is alkyl of up to 4 carbon atoms.

7. Compound as claimed in claim 1 wherein R$^1$ is alkoxy of up to 4 carbon atoms.

8. Compound as claimed in claim 1 wherein R$^2$ is hydrogen.

9. Compound as claimed in claim 1 wherein R$^2$ is alkyl of up to 4 carbon atoms.

10. Compound as claimed in claim 1 wherein R$^2$ is alkoxy of up to 4 carbon atoms.

11. Compound as claimed in claim 1 wherein R$^2$ is halogen.

12. Compound as claimed in claim 1 wherein R$^3$ is hydrogen.

13. Compound as claimed in claim 1 wherein R$^3$ is alkyl of up to 4 carbon atoms.

14. Compound as claimed in claim 1 wherein R$^3$ is alkoxy of up to 4 carbon atoms.

15. Compound as claimed in claim 1 wherein R$^3$ is halogen.

16. Compound as claimed in claim 1 wherein R$^4$ is hydrogen.

17. Compound as claimed in claim 1 wherein R$^4$ is alkyl of up to 4 carbon atoms.

18. Compound as claimed in claim 1 wherein R$^5$ is hydrogen.

19. Compound as claimed in claim 1 wherein R$^5$ is alkyl of up to 4 carbon atoms.

20. Compound as claimed in claim 1 wherein R$^5$ is alkoxy of up to 4 carbon atoms.

21. Compound as claimed in claim 1 wherein R$^5$ is alkylthio of up to 4 carbon atoms.

22. Compound as claimed in claim 1 wherein R$^5$ is dialkylamino with up to 4 carbon atoms in each alkyl group.

23. Compound as claimed in claim 1 wherein R$^5$ is halogen.

24. Compound as claimed in claim 1 wherein R$^5$ is cyano.

25. Compound as claimed in claim 1 wherein R$^5$ is alkoxycarbonyl of up to 4 carbon atoms in the alkoxy group.

26. Compound as claimed in claim 1 wherein

R$^1$ is hydrogen, alkyl or alkoxy of up to 4 carbon atoms;

R$^2$ is hydrogen, alkyl or alkoxy with up to 4 carbon atoms, fluorine, chlorine or bromine;

R$^3$ is alkyl or alkoxy with up to 4 carbon atoms, fluorine, chlorine or bromine;

R$^4$ is hydrogen or alkyl with up to 4 carbon atoms;

R$^5$ is hydrogen, alkyl, alkoxy with up to 4 carbon atoms, alkoxycarbonyl with up to 4 carbon atoms in the alkoxy group, dialkylamino with up to 4 carbon atoms in the alkyl group, fluorine, chlorine, bromine or cyano; and Z is chlorine, bromine or iodine.

27. Compound as claimed in claim 1 designated 2-ethyl-6-methyl-N-(4-methyl-1,2,5-thiadiazol-3-yl-methyl)chloroacetanilide.

28. Compound as claimed in claim 1 designated 2-ethyl-6-methyl-N-(4-methyl-1,2,5-oxadiazol-3-yl-eth-1-yl)chloroacetanilide.

29. Compound as claimed in claim 1 designated 2,6-diethyl-N-(4-methyl-1,2,5-thiadiazol-3-yl-methyl)-chloroacetanilide.

30. Compound as claimed in claim 1 designated 2-ethyl-6-methyl-N-(4-methyl-1,2,5-oxadiazol-3-yl-methyl)chloroacetanilide.

31. Compound as claimed in claim 1 designated 2,6-dimethyl-N-(4-methyl-1,2,5-oxadiazol-3-yl-methyl)-chloroacetanilide.

32. Herbicidal composition comprising a herbicidally acceptable carrier and, in herbicidally effective amounts, an N-(2,5-diazolyl)alkyl-haloacetanilide compound as claimed in claim 1.

33. Method of combating weeds which method comprises applying to the weeds, or their habitat a herbicidally effective amount of an N-(2,5-diazolyl)alkyl-haloacetanilide compound as claimed in claim 1.

34. Method as claimed in claim 33 wherein said N-(2,5-diazolyl)alkyl-haloacetanilide compound is selected from 2-ethyl-6-methyl-N-(4-methyl-1,2,5-thiadiazol-3-yl-methyl)-chloroacetanilide;

2-ethyl-6-methyl-N-(4-methyl-1,2,5-oxadiazol-3-yl-eth-1-yl)-chloroacetanilide;

2,6-diethyl-N-(4-methyl-1,2,5-thiadiazol-3-yl-methyl)-chloroacetanilide;

2-ethyl-6-methyl-N-(4-methyl-1,2,5-oxadiazol-3-yl-methyl)-chloroacetanilide; and 2,6-dimethyl-N-(4-methyl-1,2,5-oxadiazol-3-yl-methyl)-chloroacetanilide.

35. Method as claimed in claim 34 wherein said compound is applied at a dosage of 0.1 to 10 kg per hectare.

36. Method as claimed in claim 35 wherein said compound is applied at a dosage of 0.25 to 5 kg per hectare.

37. Herbicidal composition as claimed in claim 32 containing from 0.1 to 95% of the active compound, by weight.

38. Compound as claimed in claim 1 wherein:

A is sulfur;

R$^1$, R$^2$, R$^4$ and R$^5$ are separately selected from hydrogen or alkyl with up to 4 carbon atoms;

R$^3$ is hydrogen; and

Z is chlorine or bromine.

* * * * *